United States Patent [19]

Manners

[11] 4,413,354
[45] Nov. 1, 1983

[54] X-RAY DIFFRACTION CAMERA

[75] Inventor: Vincent J. Manners, New South Wales, Australia

[73] Assignee: Commonwealth of Australia, Canberra, Australia

[21] Appl. No.: 231,081

[22] Filed: Feb. 3, 1981

[30] Foreign Application Priority Data

Feb. 5, 1980 [AU] Australia .............................. PE2248

[51] Int. Cl.³ ........................................... G01M 23/20
[52] U.S. Cl. ........................................ 378/81; 378/75
[58] Field of Search ....................... 378/75, 79, 80, 81

[56] References Cited

U.S. PATENT DOCUMENTS 3,626,185 12/1971 Parrish .................................. 378/75
3,631,240 12/1971 Hoppe .................................. 378/81

Primary Examiner—Craig E. Church
Attorney, Agent, or Firm—Ladas & Parry

[57] ABSTRACT

An X-ray diffraction camera having a hypocycloidal gear train adapted to cause rotation of the sample within the camera about two generally normal axes.

4 Claims, 4 Drawing Figures

X-RAY DIFFRACTION CAMERA

The present invention relates to cameras for x-ray diffraction analysis of crystalline samples to determine lattice parameters of a sample. Still further, the present invention also relates to x-ray goniometers.

Known cameras utilize an x-ray collimating system which directs a narrow beam of x-radiation at a specimen with a resulting x-ray diffraction pattern of the specimen obtained on film. One particular system is known as the powder diffraction technique. Similar techniques are described in U.S. Pat. Nos. 3,189,741, 3,944,823, 3,509,336, 3,631,240, 3,566,112, 3,189,741, 3,564,240, 3,714,426 and 3,728,541.

The essential feature of the powder diffraction technique is that a narrow beam of monochromatic x-rays impinge upon a crystalline powder composed of fine, randomly oriented particles-ideally, all possible orientations of all possible lattice planes are present so that the x-ray beam will always find some crystallites of the proper orientation to fulfil the Bragg condition for reflection. In practice, to ensure the existence of a sufficient number of the required orientations to give a usable film from a Debye Scherrer camera, it is usually necessary to rotate, oscillate or otherwise move very small samples continuously during exposure. However, a single crystal, i.e. one whose lattice planes are all fixed with respect to any chosen edge of the crystal, cannot give a powder pattern as only a very few of its lattice planes will be in a position to reflect the x-rays according to the Bragg Law, and hence the x-ray picture will consist of a number of spots apparently randomly oriented. There is a definite need for an instrument that will yield x-ray diffraction patterns useful for identification purposes from larger single crystals, coarse crystalline aggregates, fibers or very small samples, and preferably the powder-type patterns because there is so much information available in the powder diffraction data files.

A number of attempts have been made to produce such an x-ray camera, but all have their limitations, e.g. Switzer and Holmes, (Amer. Miner 32, 1947), produced a camera which gave only some of the back reflection lines on a rotating film holder. J. Gracher and D. A. Helinek, (Norelco Reporter XIII (3) 1966) used the normal Debye-Scherrer camera and by means of an air stream, levitated and spun a sample which had been ground into a spherical shape in the x-ray beam. G. Gandolfi, (Miner. Petrogr. Acta 13 pp 67-74) used a Debye-Scherrer camera which contained two sample holders, the first of which was inclined at 45° to the vertical axis, and was rotated around the vertical axis; after the initial exposure was made in this fashion, the sample was then transferred to a vertical sample holder and a second exposure made using the usual Debye-Scherrer technique. Unless the sample is placed precisely concentric with the original sample, variations occur in both the positions and intensity of the diffraction lines.

It is an object of the present invention to overcome or substantially ameliorate the above disadvantages.

There is disclosed herein an x-ray camera comprising a sample mounting including a sample support to position the sample at a predetermined location, means to receive and support a film, means to direct x-rays at the sample so that scattered rays leaving said sample expose said film, and drive means to rotate said sample about two generally normal axes intersecting at said location, said drive means including a hypocycloidal gear train having a base gear to which said mounting is attached, said base gear being rotatable about one of said axes, and a planetary gear meshingly engaged with said base gear and wherein said sample support is coupled to said planetary gear so as to be rotated about the other axis.

A preferred form of the present invention will now be described by way of example with reference to the accompanying drawings, wherein.

Figure 1:
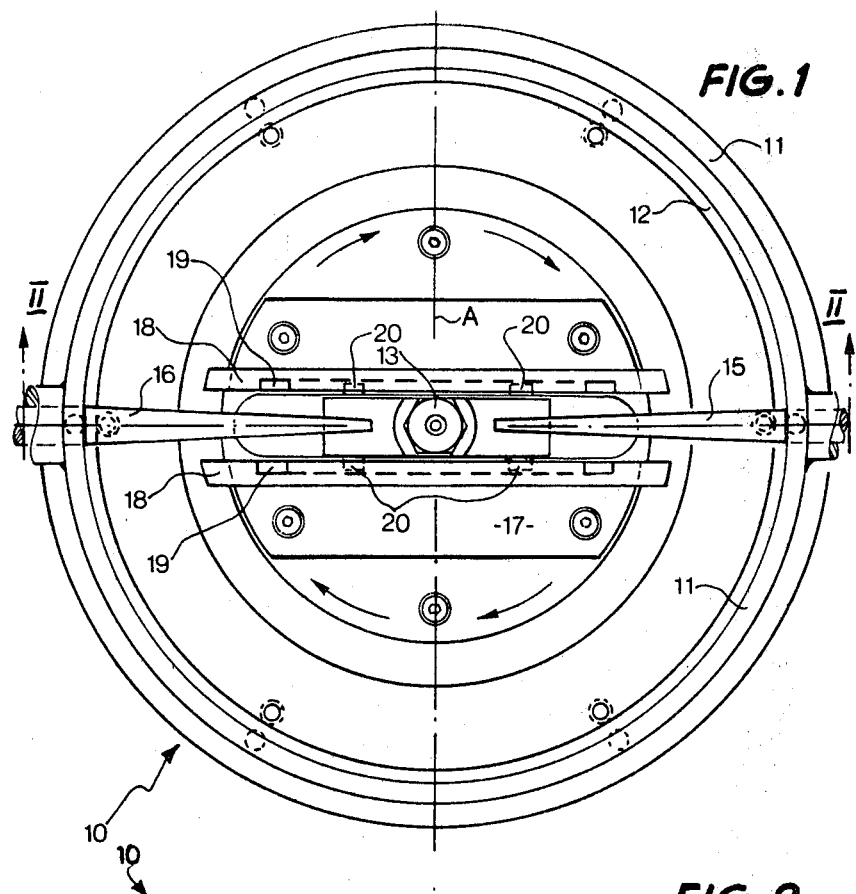
FIG. 1 is a schematic plan view of an x-ray camera.
Figure 2:
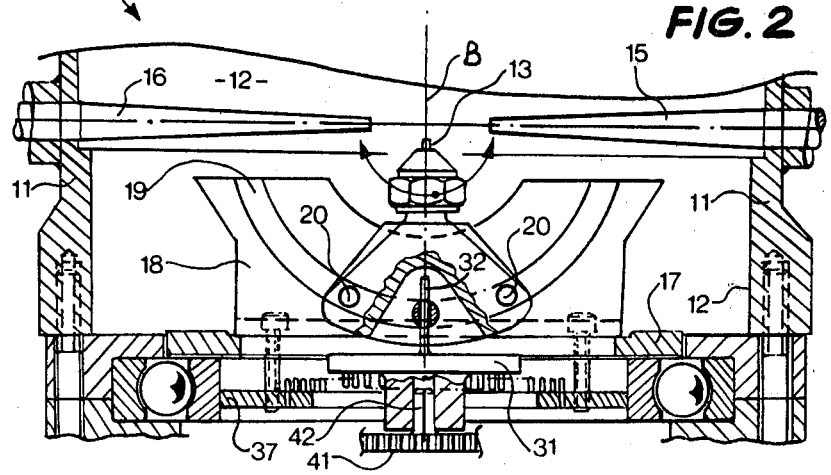
FIG. 2 is a schematic sectioned side elevation of the camera of FIG. 1.

In FIGS. 1 and 2 there is depicted a camera 10 which has a cylindrical housing 11 with an internal wall 12 to receive a strip of film. The film is looped to form a cylinder and placed against the wall 12. The film holds itself against the wall under the influence of its own resilience and is locked in this position by a sliding catch (not illustrated). Located within the housing 11 is a sample mounting 13 which positions a sample at a predetermined position defined by the intersection of the horizontal axis A and the vertical axis B. The mounting 13 includes a holder 14 which receives the sample. The sample is subjected to a narrow beam of monochromatic x-rays with the result that x-rays will be scattered by reflecting planes, these scattered rays impinge upon the film. The x-rays are directed at the sample via the primary collimator 15 while the x-rays not deflected are gathered by the receiving collimator 16. The axis B is maintained normal to the axis of the x-ray beam passing between the two collimators 15 and 16.

In order to obtain the most accurate pattern on the film, the sample should theoretically be randomly rotated about its centre, however, this theoretical requirement is approximated by rotating the sample about the axes A and B by rotating the holder 14. To achieve this the mounting has a holder base 17 which is supported by guides 18. The guides 18 include arcuate channels 19 whih have their centre at the above discussed predetermined location. Fixed to the base 17 are pins 20 which are slidingly received in channels 19. Thus the holder 14 is permitted to oscillate in a rocking motion about the axis A through an angle of 90°. To provide for the rotation about axis B the guides 18 are mounted on a rotatable base 21. Optimum results can be obtained when the rate of rotation about axis B is much greater than the oscillating rate about axis A. In this way all possible lattice planes are made to pass through the x-ray beam and hence fulfil the Bragg conditions for reflection or scattering.

Although there are many drive mechanisms which would enable the above rotational requirements to be met, it is advantageous to use a planetary gear train with a radius (and thus velocity or drive) ratio of 2:1, this functioning as a hypocycloidal generator which results in a point of the rolling circle generating a straight line whose length is the diameter of the base circle. Additionally, to further approximate a random motion, prime number gear ratios are used, hence coincidence occurs only after a large number of oscillations. Thus the motion of the sample with respect to the beam is virtually random.

Figure 3:
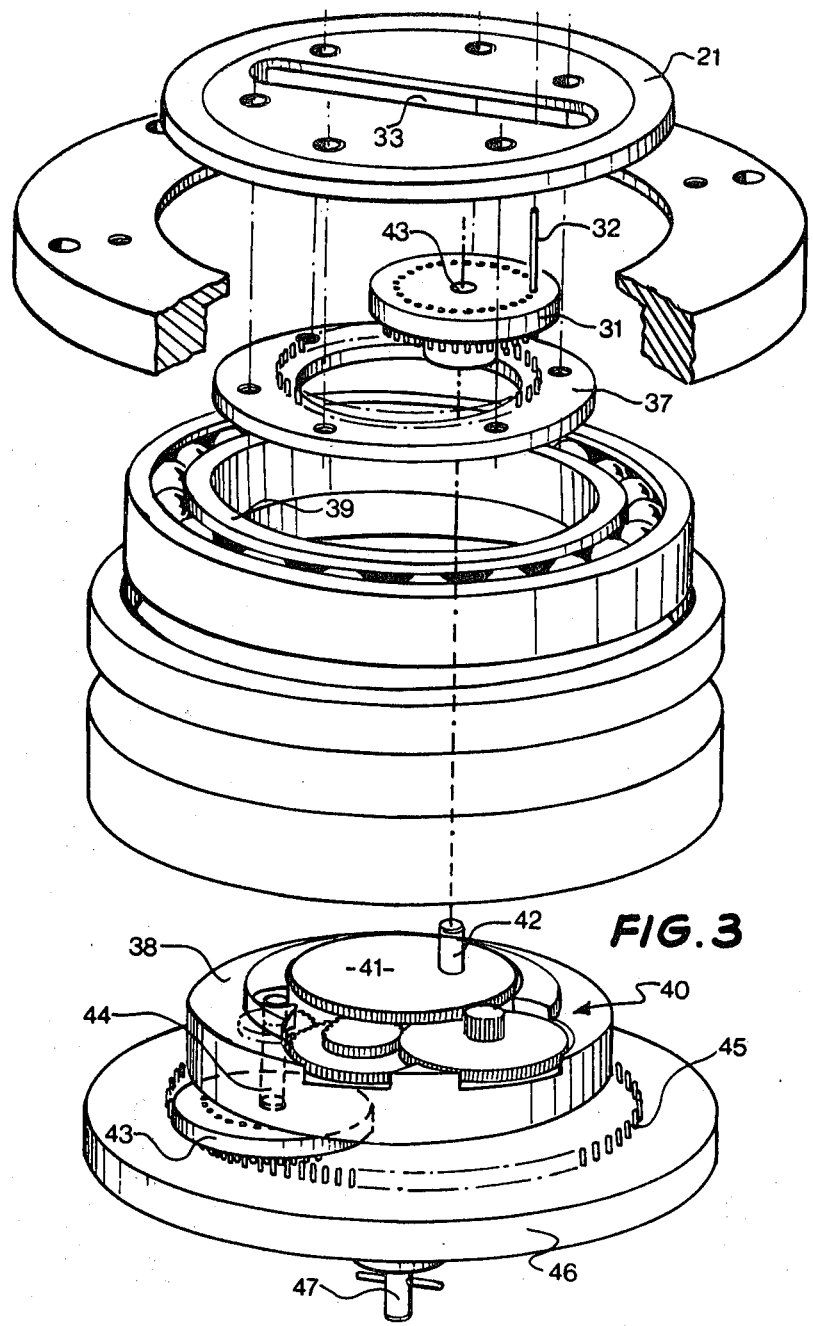
FIG. 3 is a schematic exploded parts view of a drive for the sample mounting employed in the camera of FIG. 1.

In FIG. 3 there is depicted a gear train 30 which can be used to drive the sample holder 14. The gear train 30 includes a gear 31 (see FIG. 2) which is coupled by vertical link 32 to base 17. The gear 31 is rotated about its own axis as well as circling the axis B in a planetary motion. The link 32 moves back and forth in the slot 33 while the slot 33 is rotated about the axis A since the base 21 is fixed to the gear 37. Additionally the link is slidable through the gear 31. The base 21 is driven by the gear 37 which in turn is fixed to a carrier 38. The gear 37 is rotatably supported by the inside race of the ball bearing 39 while the outer race is supported by the housing 11.

Supported on the carrier 38 is a reduction gear train 40 which includes an output gear 41 having a pin 42 which is engaged within the central passage 43 of the gear 31 so as to rotatably support same while moving the gear 31 in a planetary action around the central axis of the gear 37. The reduction gear train 40 has an input gear 43 which is rotatably supported by means of a shaft 44 mounted in the carrier 38. The gear 43 meshingly engages a gear 45 formed on the bottom portion 46 of the housing 11. The portion 46 is stationary. Fixed to the carrier 38 is a drive input shaft 47 whose rotation also causes rotation of the carrier 38 and the subsequent movement of the gear 43 about the central axis of the carrier 38 to thereby cause rotation of the gear 43 about the axis of the shaft 44. This in turn via the reduction gear train 40 causes rotation of the pin 42 about the central axis of the gear 37.

Additionally, since the base 21 is fixed to the gear 37 which in turn is fixed to the carrier 38, the shaft 47 thereby causes rotation of the base 21. Since there is a direct coupling of the base 21 to the shaft 47, the base 21 rotates at the same angular velocity, while due to the reduction gear 40, the gear 31 rotates at a much lower angular velocity about the pin 42 and about the central axis of the gear 37. Thus the angular velocity of the holder 14 about the axis B is far greater than the angular velocity of the holder 14 about the axis A.

Figure 4:
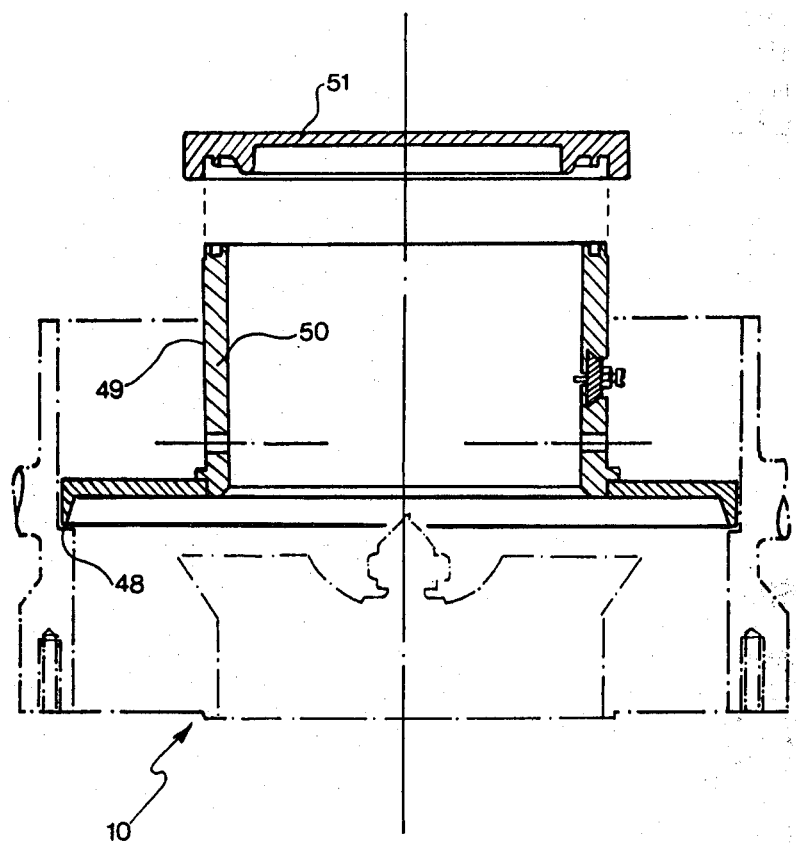
FIG. 4 is a schematic sectioned side elevation of the camera of FIG. 1 with an adapter to expose a smaller film.

Now with reference to FIG. 4, the camera 10 is provided with a lip 48 upon which an adapter 49 rests, which adapter receives a film on its internal surface 50 so that a smaller film may be employed. A cover 51 is provided for the adapter 49.

What I claim is:

1. An x-ray camera comprising a sample mounting including a sample support to position the sample at a predetermined location, means to receive and support a film, means to direct x-rays at the sample so that scattered rays leaving said sample expose said film, and drive means to rotate said sample about two generally normal axes intersecting at said location, said drive means including a hypocycloidal gear train having a base gear to which said mounting is attached, said base gear being rotatable about one of said axes, and a planetary gear meshingly engaged with said base gear and wherein said sample support is coupled to said planetary gear so as to be rotated about the other axis.

2. The camera of claim 1 wherein said sample mounting comprises guide means having an arcuate slot having a centre coincident with said other axis, said sample support having engaging means located within said slot, said planetary gear has a projection slidably engaged within said support so that linear motion executed by said projection causes oscillation of said support about said other axis by movement of said engaging means within said slot.

3. The camera of claim 1 further including a reduction gear meshingly engaged with said planetary gear so that the angular velocity of said sample holder about said other axis is less than the angular velocity of said mounting about said one of said axes.

4. The camera of claim 3 further including a carrier upon which said reduction gear is mounted and wherein said sample mounting is fixed to said carrier so that rotation of said carrier causes rotation of said mounting means at the same angular velocity, and wherein said reduction gear train has an input gear meshingly engaged with a further stationary gear so that rotation of said carrier causes rotation of said input gear.

* * * * *